(12) United States Patent
Hwang et al.

(10) Patent No.: US 10,597,670 B2
(45) Date of Patent: Mar. 24, 2020

(54) PHD GENE INVOLVED IN DEVELOPMENT AND FORMATION OF PLANT PHLOEM

(71) Applicant: POSTECH ACADEMY-INDUSTRY FOUNDATION, Pohang-si, Gyeongsangbuk-do (KR)

(72) Inventors: Ildoo Hwang, Pohang-si (KR); Joonseon Yoon, Daejeon (KR); Ho Jin Ryu, Suwon-si (KR); Hyunwoo Cho, Pohang-si (KR)

(73) Assignee: POSTECH ACADEMY-INDUSTRY FOUNDATION, Pohang-si, Gyeongsang (KR)

( * ) Notice: Subject to any disclaimer, the term of this patent is extended or adjusted under 35 U.S.C. 154(b) by 146 days.

(21) Appl. No.: 15/024,384

(22) PCT Filed: May 9, 2014

(86) PCT No.: PCT/KR2014/004169
§ 371 (c)(1),
(2) Date: Mar. 24, 2016

(87) PCT Pub. No.: WO2015/046700
PCT Pub. Date: Apr. 2, 2015

(65) Prior Publication Data
US 2016/0244778 A1    Aug. 25, 2016

(30) Foreign Application Priority Data

Sep. 24, 2013 (KR) .......................... 10-2013-0113544

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

U.S. PATENT DOCUMENTS

| 4,940,838 A | 7/1990 | Schilperoort et al. | |
| 2010/0218271 A1* | 8/2010 | Sanz Molinero | .... C07K 14/415 800/278 |

FOREIGN PATENT DOCUMENTS

| EP | 0 120 516 B1 | 10/1984 | |
| EP | 0 301 316 B1 | 2/1989 | |
| KR | 10-2010-0090354 A | 8/2010 | |
| KR | 10-2010-0127467 A | 12/2010 | |
| KR | 10-2012-0041608 A | 5/2012 | |
| WO | WO 2008/015263 A2 * | 2/2008 | |
| WO | WO-2008015263 A2 * | 2/2008 | ........... C07K 14/415 |

OTHER PUBLICATIONS

Pandey et al. Virology journal 6.1 (2009): 152, 1-13.*
Pandey et al. Virology journal 6.1 (2009): 152,1-13. (Year: 2009).*
Bonke et al., "APL regulates vascular tissue identity in *Arabidopsis*", Nature, vol. 426, pp. 181-186, (2003).
Truernit et al., "OCTOPUS, a polarly localised membrane-associated protein, regulates phloem differentiation entry in *Arabidopsis thaliana*", Development, vol. 139, pp. 1306-1315, (2012).
Cano-Delgado et al., "BRL1 and BRL3 are novel brassinosteroid receptors that function in vascular differentiation in *Arabidopsis*", Development, vol. 131, pp. 3445-3455, (2004).
Krens et al., "In vitro transformation of plant protoplasts with Ti-plasmid DNA", Nature, vol. 296, pp. 72-74, (1982).
Negrutiu et al., "Hybrid genes in the analysis of transformation conditions", Plant Mol. Biol., vol. 8, pp. 363-373, (1987).
Shillito et al., "High Efficiency Direct Gene Transfer to Plants", Bio/Technol., vol. 3, pp. 1099-1102, (1985).
Crossway et al., "Integration of foreign DNA following microinjection of tobacco mesophyll protoplasts", Mol. Gen. Genet., vol. 202, pp. 179-185, (1986).
Klein et al., "High-velocity microprojectiles for delivering nucleic acids into living cells", Nature, vol. 327, pp. 70-73, (1987).
Masiero et al., "INCOMPOSITA: a MADS-box gene controlling prophyll development and floral meristem identity in Antirrhinum", Development, vol. 131, pp. 5981-5990, (2004).
Bendahmane et al., "The Rx Gene from Potato Controls Separate Virus Resistance and Cell Death Responses", Plant Cell, vol. 11, pp. 781-791, (1999).
GenBank Accession No. NP_188189, RAN BP2/NZF zinc finger-like protein [*Arabidopsis thaliana*], (May 28, 2011).
GenBank Accession No. NP_197931, Ran BP2/NZF zinc finger-like protein [*Arabidopsis thaliana*], (May 28, 2011).

* cited by examiner

Primary Examiner — Charles Logsdon
(74) Attorney, Agent, or Firm — Vorys, Sater, Seymour & Pease LLP; Mih Suhn Koh

(57) ABSTRACT

Disclosed is a PHD protein regulating the differentiation of plant phloem; a recombinant vector containing a gene encoding the same; a plant transformed with the recombinant vector; a seed of the plant; and a method for regulating the development and formation of plant phloem by using the gene encoding the PHD protein. Regulated is the development of phloem, which plays the role in moving a photosynthetic product and finally storing the same in starch and sugar forms in a plant storage organ, so as to regulate the function of phloem, thereby having an effect of controlling the size and storage capacity of the plant storage organ. The development of phloem can be improved by allowing the PHD gene to be silent in plants, and thus it is expected that the function of plant phloem can be increased through the regulation of PHD gene expression by using genetic engineering techniques.

3 Claims, 6 Drawing Sheets

Specification includes a Sequence Listing.

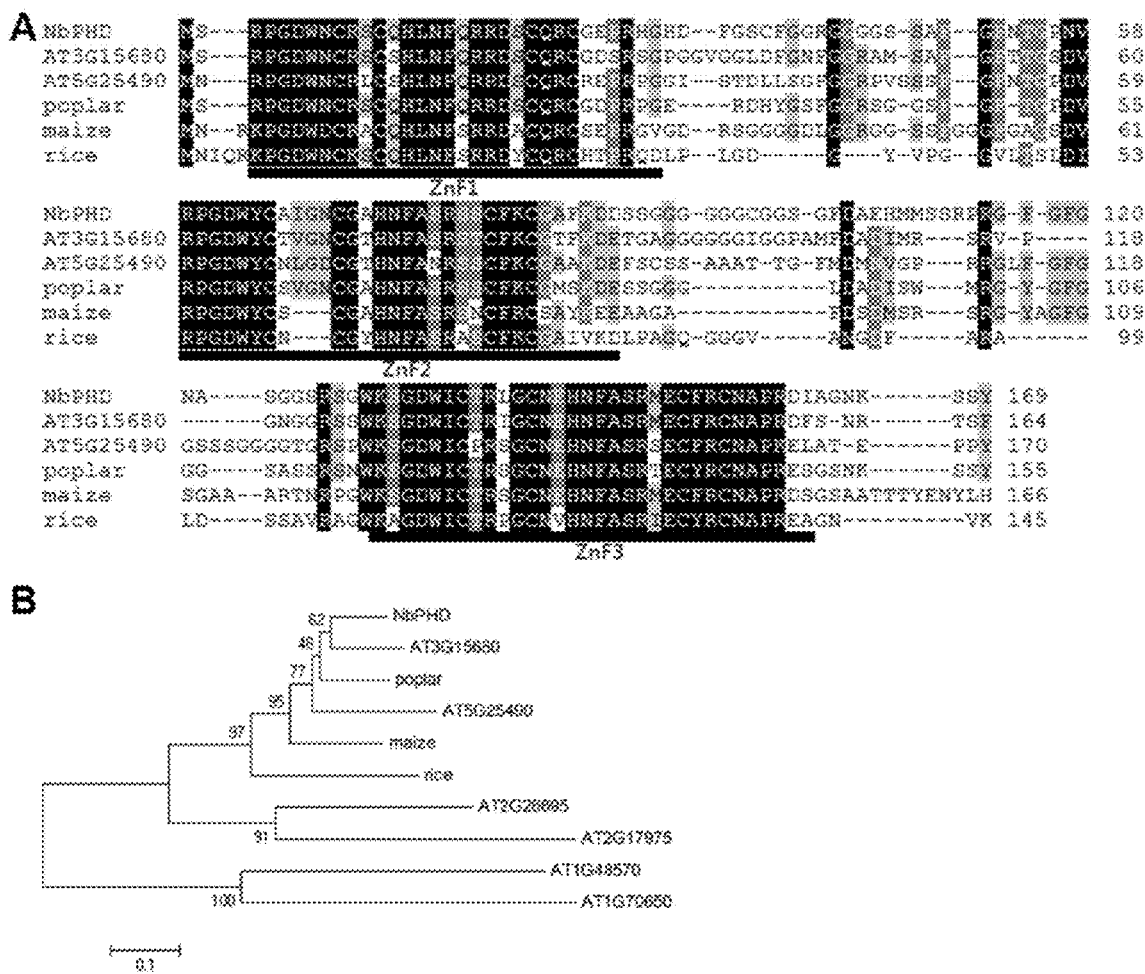
[Fig. 1]
At3G15680 – SEQ ID NO: 1
At5G25490 – SEQ ID NO: 2
NbPHD – SEQ ID NO: 5
Poplar – SEQ ID NO: 6
Maize – SEQ ID NO: 7
Rice – SEQ ID NO: 8

[Fig. 2]
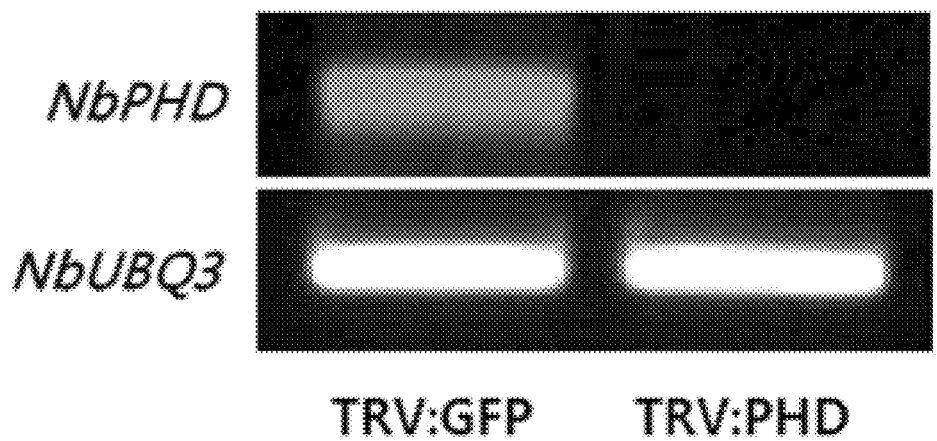

[Fig. 3]
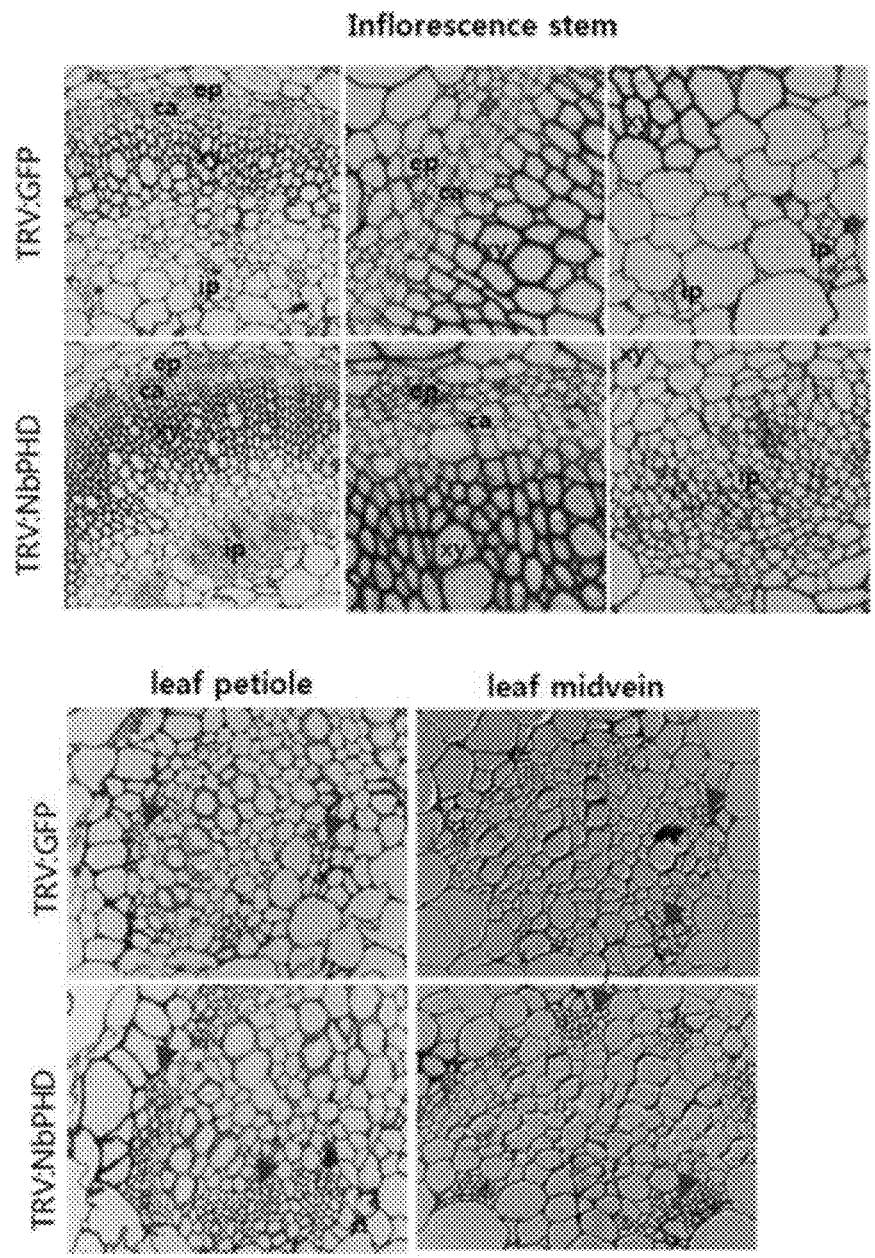

[Fig. 4]
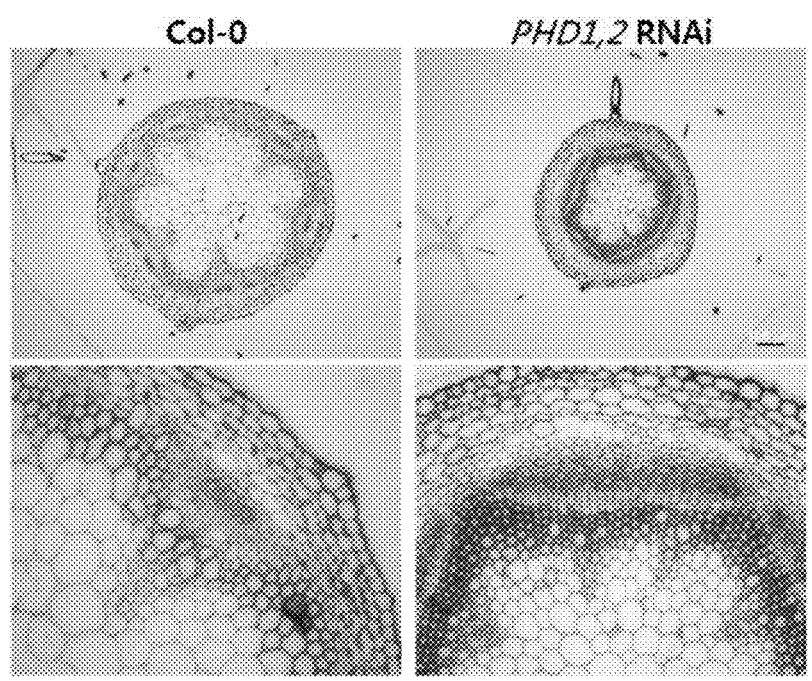

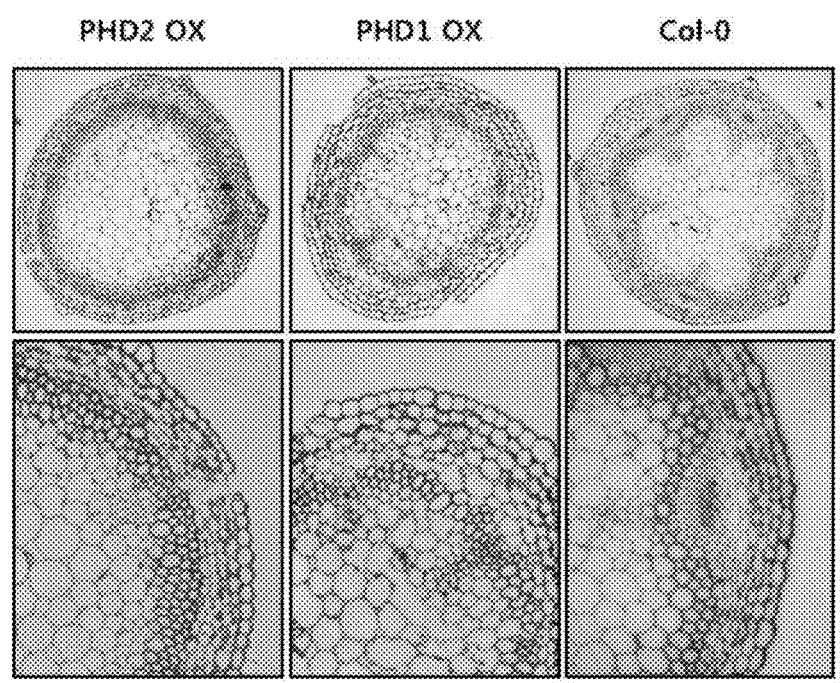
[Fig. 5]

[Fig. 6]
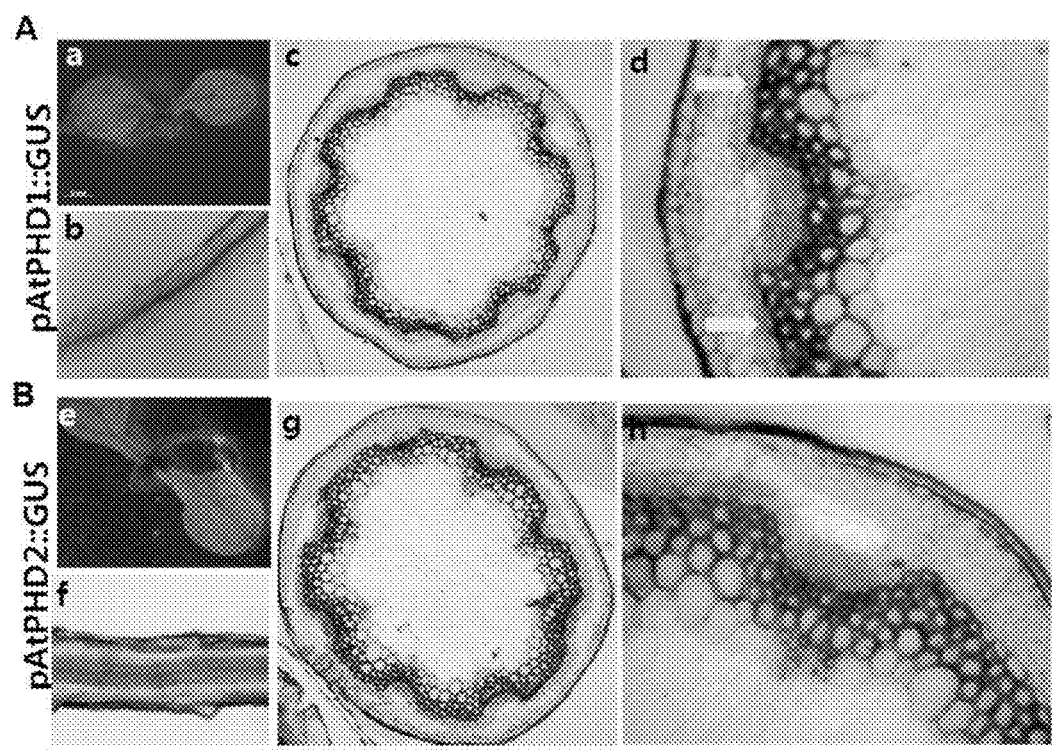

PHD GENE INVOLVED IN DEVELOPMENT AND FORMATION OF PLANT PHLOEM

Statement Regarding Government Rights

The present invention was undertaken with the support of Development of techniques for controlling energy distribution through key regulators in phloem development No. 2014R1A2A1A10052592 grant funded by the Ministry of Science, ICT and Future Planning, Development of carbon metabolism engineering biotechnology to improve yield of crop plants No. PJ010953022016 grant funded by the Rural Development Administration, and Development of transgenic plants for biomass production No. 309017-05-1-SB010 grant funded by the Ministry of Agriculture, Food and Rural Affairs.

CROSS-REFERENCE TO RELATED APPLICATION

This application is a National Phase Application filed under 35 U.S.C. 371 as a national stage of PCT/KR2014/004169, filed on May 9, 2014, and claims priority to and the benefit of Korean Patent Application No. 10-2013-0113544, filed on Sep. 24, 2013, the disclosure of which is incorporated herein by reference in its entirety.

SEQUENCE LISTING

The Sequence Listing submitted in text format (.txt) filed on Sep. 29, 2016, named "Sequencelisting.txt", created on Sep. 26, 2016, 10.0 KB), is incorporated herein by reference.

TECHNICAL FIELD

The present invention relates to a PHD protein regulating the differentiation of the phloem of a plant, a recombinant vector including a gene encoding the same, a plant transformed with the recombinant vector, a seed of the plant, and a method of regulating the development and formation of the phloem of the plant using the gene encoding the PHD protein.

BACKGROUND ART

In plants, the phloem is a vital plant organ for regulating the development of each plant organ through movement of photosynthetic products and particularly, for accumulating the photosynthetic products in plant storage organs which human beings need. The phloem differentiates into sieve elements through which photosynthetic products directly move from procambium stem cells inducing the formation of vascular bundles, companion cells known to supply ATPs, proteins, and the like to the sieve elements. The sieve elements and the companion cells make pairs to promote the movement of the photosynthetic products.

Also, the plant phloem is an organ that plays the most important role in moving products synthesized in photosynthesis to storage organs of the plant. The plant storage organs have much agricultural and economic importance as a fodder for animals. That is, when the functions of the phloem are improved, it is expected to achieve more efficient movement of photosynthetic products to the plant storage organs, thereby increasing the yield of crops.

However, very little is known about genes involved in the formation of the phloem so far, and only a few related genes have just been identified by genetic experiment methods using a plant model of *Arabidopsis thaliana*. Among the known genes, an APL gene is an important gene to induce the phloem formation, and thus it has been reported that the phloem is not formed when this gene is knocked out (Bonke et al., 2003, Nature 426:181-186). Also, in the case of a newly identified gene named "OCTOPUS", when the new gene has problems with gene functions, it has been reported that the differentiation of cambium cells into differentiated cells of the phloem is delayed (Truernit et al., 2012, Development 139:1306-1315). In addition, it has been reported that the number of the phloem cells slightly increases when the signaling and biosynthesis of brassinosteroids as plant hormones are problematic in a mechanism of regulating the number of the phloem cells (Cano-Delgado et al., 2004, Development 131:3445-3455). However, there has been almost no molecular-level research on how phloem development is controlled in plants.

Therefore, a molecular-level research on novel genes involved in regulating the development and formation of the phloem in plants is needed.

DISCLOSURE

Technical Problem

Accordingly, the present inventors have researched novel genes involved in a mechanism of regulating the formation of phloem in plants and found that PHD genes play a role in negatively regulating the phloem formation in the plants. Therefore, the present invention has been completed based on these facts.

Therefore, it is an aspect of the present invention to provide a recombinant virus induced gene silencing (VIGS) vector including a gene encoding a PHD protein.

It is another aspect of the present invention to provide a plant transformed with the recombinant VIGS vector and having an increased phloem formation.

It is still another aspect of the present invention to provide a seed of the plant having increased phloem formation.

It is yet another aspect of the present invention to provide a method of increasing phloem formation in a plant, which includes transforming a plant with a recombinant VIGS vector including a gene encoding a PHD protein to silence a PHD gene.

However, the problems to be solved according to the present invention are not limited to the above-described problems, and other problems which are not disclosed herein may be made apparent to those skilled in the art by the detailed description provided below.

Technical Solution

To solve the above problems, according to an aspect of the present invention, there is provided a recombinant virus induced gene silencing (VIGS) vector including a gene encoding a PHD protein.

According to another aspect of the present invention, there is provided a plant transformed with the recombinant VIGS vector and having an increased phloem formation.

According to still another aspect of the present invention, there is provided a seed of the plant having an increased phloem formation.

According to yet another aspect of the present invention, there is provided a method of increasing phloem formation in a plant, which includes transforming a plant with a recombinant VIGS vector comprising a gene encoding a PHD protein to silence a PHD gene.

According to one exemplary embodiment of the present invention, the method of increasing phloem formation in the plant may include inserting a gene encoding a PHD protein into a VIGS vector, transforming *Agrobacterium* sp. with the constructed vector, and infiltrating a plant with the transformed *Agrobacterium* sp.

According to another exemplary embodiment of the present invention, the PHD protein may have an amino acid sequence set forth in SEQ ID NO: 1 or SEQ ID NO: 2.

According to still another exemplary embodiment of the present invention, the plant may be selected from the group consisting of food crops including rice, wheat, barley, corn, bean, potato, Indian bean, oats, and Indian millet, vegetable crops including *Arabidopsis thaliana*, Chinese cabbage, radish, red pepper, strawberry, tomato, watermelon, cucumber, cabbage, oriental melon, pumpkin, Welsh onion, onion, and carrot, special crops including ginseng, a tobacco plant, a cotton plant, sesame, sugar cane, sugar beet, *Perilla* sp., peanut, and rape, fruit trees including an apple tree, a pear tree, a jujube tree, a peach tree, a kiwi fruit tree, a grape tree, a citrus fruit tree, a persimmon tree, a plum tree, an apricot tree, and a banana tree, flower crops including rose, gladiolus, gerbera, carnation, chrysanthemum, lily, and tulip, and fodder crops including ryegrass, red clover, orchard-grass, alfalfa, tall-fescue, and perennial ryegrass.

Advantageous Effects

The present invention provides a recombinant VIGS vector including a PHD gene which negatively regulates the development of phloem that is an organ that plays the most important role in delivering photosynthetic products and finally storing the photosynthetic products in the form of starch and sugar in storage organs in a plant and thus can have an effect of regulating the functions of the phloem to control the size and storage capacity of the storage organs in the plant. Therefore, it is anticipated that a mechanism of regulating the differentiation of the phloem by the PHD gene will be useful in improving crops and enhancing production of terrestrial biomass in the future.

DESCRIPTION OF DRAWINGS

FIG. 1 is a diagram showing whether similar genes exist in various plant species to determine a structure of a PHD gene.

FIG. 2 is a diagram showing the results of silencing a PHD gene in a tobacco plant using a virus-induced gene silencing (VIGS) system.

FIG. 3 is a diagram showing the results of observing cells of external phloem (ep) and internal phloem (ip) regions in flower stalks and leaf veins of a tobacco plant whose PHD gene has been silenced.

FIG. 4 is a diagram showing the results of observing vascular tissues of a plant *Arabidopsis thaliana* whose PHD1 and PHD2 genes have been knocked down.

FIG. 5 is a diagram showing the results of observing whether a developmental change of the phloem is caused when the PHD1 and PHD2 genes of *Arabidopsis thaliana* are overexpressed.

FIG. 6 is a diagram showing the results of observing which regions of the PHD gene of *Arabidopsis thaliana* are expressed.

BEST MODE

The present inventors have found that the formation of phloem is remarkably inhibited when PHD1 and PHD2 genes are overexpressed in a plant, and the formation of phloem is increased when these genes are knocked down. Therefore, the present invention has been completed based on these facts.

Accordingly, the present invention is characterized by providing a recombinant virus induced gene silencing (VIGS) vector including a gene encoding a PHD protein.

In the present invention, the PHD protein includes a PHD1 protein having an amino acid sequence set forth in SEQ ID NO: 1 or a PHD2 protein having an amino acid sequence set forth in SEQ ID NO: 2, and functional equivalents of the proteins. The term "functional equivalent" refers to a protein which has a sequence homology of at least 70% or more, preferably 80% or more, more preferably 90% or more, and most preferably 95% or more with the amino acid sequence set forth in SEQ ID NO: 1 or SEQ ID NO: 2 as a result of addition, substitution or deletion of amino acids and thus exhibits substantially the same biological activity as the protein set forth in SEQ ID NO: 1 or SEQ ID NO: 2. The term "substantially the same biological activity" refers to an activity to form the phloem in a plant.

Also, in the present invention, the gene encoding the PHD protein includes all genomic DNAs and cDNAs encoding PHD proteins. Preferably, the gene according to one exemplary embodiment of the present invention may be a PHD1 gene having a base sequence set forth in SEQ ID NO: 3, or a PHD2 gene having a base sequence set forth in SEQ ID NO: 4. The base sequence of SEQ ID NO: 3 refers to a sequence encoding the protein having an amino acid sequence of SEQ ID NO: 1, and the base sequence of SEQ ID NO: 4 refers to a sequence encoding the protein having an amino acid sequence of SEQ ID NO: 2. Also, variants of the base sequence are encompassed within the scope of the present invention. Specifically, the gene may include a base sequence having a sequence homology of 70% or more, more preferably 80% or more, further preferably 90% or more, and most preferably 95% or more with the base sequence of either SEQ ID NO: 3 or SEQ ID NO: 4. The sequence homology (%) between polynucleotides is determined by comparing a comparison region with two optimally aligned sequences. In this case, some of a polynucleotide sequence in the comparison region may include additions or deletions (that is, gaps) compared to a reference sequence (having no additions or deletions) for optimal alignment of the two sequences.

Meanwhile, virus-induced gene silencing (VIGS) as a gene silencing condition induced by viruses is also referred to as virus-induced RNA silencing. The VIGS may be a kind of a post-transcriptional gene silencing condition widely known in various plants, fungi, insects, nematodes, fishes, mice, etc., that is, a condition in which when an endogenous gene homologous with a viral genome is expressed in an infected plant, expression and replication of both the endogenous gene and the viral genome are suppressed together during an invasion of viruses into a plant and replication of the viruses. That is, when some or all of a certain gene derived from a host is inserted into cDNA of the viral genome and constructed as an infectious RNA and a plant is infected with the gene, RNAs of the corresponding host are targeted, thereby suppressing or eliminating the expression of a target gene in the infected host plant. As a result, the functions of the target gene may be indirectly estimated. A VIGS mechanism is known as a kind of a plant defense mechanism which is mediated by RNAs against viruses and has characteristics such as 1) post-transcriptional gene silencing 2) RNA conversion, and 3) nucleotide sequence specificity.

According to one exemplary embodiment of the present invention, the present inventors have successfully inhibited expression of the PHD gene by inserting a Ti plasmid into *Agrobacterium* sp. using a tobacco rattle virus (TRV) that is a transformant VIGS vector and infiltrating a plant with the *Agrobacterium* sp. (see FIG. 2).

In the present invention, the term "recombinant" refers to a cell which replicates or expresses xenogeneic nucleic acids, or a cell which expresses a protein encoded by a peptide, a xenogeneic peptide, or xenogeneic nucleic acids. Recombinant cells may express a gene or gene fragments which have not been found in the wild-type form of the cells in either the sense or antisense form. Also, the recombinant cells may express genes found in the wild-type cells, but the genes are modified and re-introduced into the cells using artificial means. In addition, term "vector" may be used to refer to a DNA fragment(s) or a nucleic acid molecule to be delivered into the cells. The vector may replicate and independently reproduce DNAs in host cells.

In the present invention, a preferred example of the recombinant vector is a Ti-plasmid vector that may transfer a portion thereof, that is, a T-domain, to plant cells when present in a proper host such as *Agrobacterium tumefaciens*. Another type of the Ti-plasmid vector is currently used to transfer a heterogeneous DNA sequence to protoplasts, which may lead to production of a new plant by properly inserting a plant cell or heterogeneous DNAs to a plant genome. An especially preferred form of the Ti-plasmid vector is a so-called binary vector as claimed in European Patent No. 0120516 and U.S. Pat. No. 4,940,838. Other proper vectors that may be used to introduce the DNAs of the present invention into a plant host may be selected from a vector which may be derived from a double-stranded plant virus (e.g., CaMV), a single-stranded plant virus, Gemini viruses, etc., for example a non-complete plant viral vector. The vector may be advantageously used when it is difficult to properly transform a plant host. Also, in the recombinant vector of the present invention, a promoter may be a CaMV 35S, actin, ubiquitin, pEMU, MAS, or histone promoter, but the present invention is not limited thereto. The term "promoter" refers to a DNA upstream region from a structural gene, that is, a DNA molecule to which a RNA polymerase binds to initiate a transcription.

Also, the present invention provides a plant and a seed thereof. Here, the plant is transformed with the recombinant VIGS vector to have increased phloem formation.

In addition, the present invention provides a method of increasing phloem formation in a plant, which includes transforming plant with a recombinant VIGS vector including a gene encoding a PHD protein to silence a PHD gene.

Transformation of the plant refers to any method by which DNAs are delivered to a plant. Such a transformation method does not necessarily have a time period for regeneration and/or tissue culture. Transformation of plant species is quite general, and thus is for not only dicot plants but also monocot plants. In principle, any transformation method may be used to introduce the DNAs of the present invention to proper progenitor cells. The method may be properly selected from a calcium/polyethylene glycol method for known protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method to plant components (Crossway A. et al., 1986, Mol. Gen. Genet. 202, 179-185), a particle bombardment method for various plants components (DNA or RNA-coated) (Klein T. M. et al., 1987, Nature 327, 70), or a (non-complete) viral infection method for transfer of an *Agrobacterium tumefaciens*-mediated gene by invasion of a plant or transformation of matured pollens or microspores (European Patent No. 0301316), etc. A preferred method according to one exemplary embodiment of the present invention includes *Agrobacterium*-mediated DNA transfer. In particular, the use of a so-called binary vector technique as disclosed in European Patent No. 0120516 and U.S. Pat. No. 4,940,838 is particularly preferred.

In the present invention, the most preferred method of increasing phloem formation in the plant may include inserting a gene encoding a PHD protein into a VIGS vector, transforming *Agrobacterium* sp. with the constructed vector, and infiltrating a plant with the transformed *Agrobacterium* sp.

Further, in the present invention, the plant may include food crops including rice, wheat, barley, corn, bean, potato, Indian bean, oats, and Indian millet; vegetable crops including *Arabidopsis thaliana*, Chinese cabbage, radish, red pepper, strawberry, tomato, watermelon, cucumber, cabbage, oriental melon, pumpkin, Welsh onion, onion, and carrot; special crops including ginseng, a tobacco plant, a cotton plant, sesame, sugar cane, sugar beet, *Perilla* sp., peanut, and rape; fruit trees including an apple tree, a pear tree, a jujube tree, a peach tree, a kiwi fruit tree, a grape tree, a citrus fruit tree, a persimmon tree, a plum tree, an apricot tree, and a banana tree; flower crops including rose, gladiolus, gerbera, carnation, chrysanthemum, lily, and tulip; and fodder crops including ryegrass, red clover, orchard grass, alfalfa, tall fescue, and perennial ryegrass.

Here, *Arabidopsis thaliana* or a tobacco plant is most preferred.

MODE FOR INVENTION

Hereinafter, preferred exemplary embodiments of the present invention will be described in order to aid in understanding the present invention. However, it should be understood that the description set forth herein is merely exemplary and illustrative of the exemplary embodiments for the purpose of describing the present invention and is not intended to limit the present invention.

Example 1

Preparation of Plant Model

To examine a structure of a PHD gene, the present inventors investigated whether similar genes exist in various plant species, found PHD homologues even in *Arabidopsis thaliana* (At3G15680, At5G25490), poplar, a monocotyledonous plant (corn) and rice as shown in FIG. 1A and confirmed that these genes specifically have a simple structure in which RanBP2-type zinc finger motifs are repeated three times. Also, the genes having the RanBP2-type zinc finger motifs were investigated in *Arabidopsis thaliana* to draw a distribution diagram for the similar genes present in the rice, corn, and poplar. As a result, it could be seen that two genes At3g15680, At5g25490 were very homologous to an NbPHD gene in *Arabidopsis thaliana* and that the other genes shared the motifs but were remote from the PHD gene, as shown in FIG. 1B.

Accordingly, the present inventors constructed an *Arabidopsis thaliana* plant in which the PHD genes (At3g15680, At5g25490) were overexpressed in *Arabidopsis thaliana* and a knock-down *Arabidopsis thaliana* plant. Here, wild-type and mutant species of *Arabidopsis thaliana* were in the Columbia (Col) background and constructed using an RNAi method known by H. Sommer (Masiero, S. et al., 2004. Development 131: 5981-5990).

Also, a tobacco plant which was transformed by a VIGS method to silence the PHD genes was constructed using a method of infiltrating *Agrobacterium* sp. using a transformant VIGS vector TRV as known in the related art (Bendahmane et al., 1999. Plant Cell 11: 781-791), and it was confirmed whether the PHD (NbPHD) gene of the tobacco plant was effectively silenced. As a result, it could be seen that a significant number of PHD transcripts was present in the control group (TRV:GFP) in which GFP was silenced, but no PHD transcripts were observed in a group (TRV:PHD) in which the PHD gene was silenced, as shown in FIG. 2.

All the plants constructed thus were grown in soil at a temperature of 23° C. under long-day (LD) conditions (16/8 hours (light/dark)-light intensity: 120 µmol m-2 s-1).

Example 2

Morphological Analysis

To perform morphological analyses for vascular tissues in the stems and leaf veins of the *Arabidopsis thaliana* and tobacco plant constructed in Example 1, first of all, the tissues were fixed in a fixative solution (3% glutaraldehyde in 0.1M sodium phosphate buffer; pH 7.2) for 3 hours. Thereafter, the tissues were plasticized using a Spurr's resin, cut into pieces having a thickness of 2 µm using a microtome apparatus, stained in a 0.025% toluidine blue solution, and then observed and imaged under a microscope.

As a result, it was revealed that the number of cells in the external phloem (ep) and internal phloem (ip) regions highly increased in the leaf veins present in the stems and leaves of the tobacco plant in which the PHD genes were silenced, as shown in FIG. 3. The phloem cells are indicated by arrows. As a result, it was confirmed that the amount of both of the external phloem and the internal phloem increased in the tobacco plant (TRV:NbPHD) in which the PHD genes were silenced, compared to the control (TRV:GFP).

Also, to examine whether the function of regulating the phloem formation found in the tobacco plant was included in the *Arabidopsis thaliana* PHD gene, the vascular tissue of a mutant *Arabidopsis thaliana* plant in which the PHD1 and PHD2 genes constructed in Example 1 were knocked down were observed. As a result, it could be seen that the number of the phloem cells significantly increased in inflorescence stems of the mutant plant (PHD1,2 RNAi), compared to wild-type Col-0 and that the vascular bundles were connected without clearly distinguishing between the vascular bundles and interfascicular cambiums were well developed, as shown in FIG. 4. From such a phenotype, it could be seen that the PHD genes were involved in inhibiting dedifferentiation of interfascicular parenchymal cells into the cambiums as well as cambium activity and differentiation from the phloem.

In addition, it was observed how the development of the phloem varied when the *Arabidopsis thaliana* PHD1 and 2 genes were overexpressed. As a result, it was found that a normal vascular bundle pattern was not observed in the PHD1/2-overexpressed plant (PHD1 OX, PHD2 OX) compared to the wild type (Col-0), and the cambiums were hardly observed even at a region in which the vascular bundles seemed to be present, as shown in FIG. 5. Also, it was revealed that the phloem cells were not observed, and the vascular bundles in which only protoxylems were morphologically present were also be observed. In some severe cases, it was revealed that the vascular bundles were not observed at all.

Example 3

GUS Expression Analysis

To analyze expression patterns of the PHD genes in *Arabidopsis thaliana* and tobacco plant grown in Example 1, each of the promoter regions of the PHD1 (At3g15680) and PHD2 (At5g25490) genes were bound to a GUS gene, and an *Arabidopsis thaliana* plant was transformed using *Agrobacterium* sp. Thereafter, to check expression of the GUS gene, the plant was stained with a GUS-dye solution (100 mM Tris-HCl (pH 7.0), 2 mM ferricyanide, 1 mM 5-bromo-4-chloro-3-indolyl-b-D-glucuronidase (X-Gluc)) for 6 hours or more.

As a result, it could be seen that the PHD genes were expressed at a seedling stage in seminal leaves and roots (see FIGS. 6A, 6B, 6E, and 6F), as shown in FIG. 6A (pAtPHD1::GUS) and FIG. 6B (pAtPHD2::GUS). Also, it could be seen that the PHD genes were expressed in the vascular bundles in the inflorescence stem and particularly expressed in the phloems and procambiums (see FIGS. 6C and 6G). Further, it was revealed that the PHD genes were also expressed in the interfascicular parenchymal cells, indicating that the tissues were dedifferentiated into the cambiums with a secondary growth of the cells (see FIGS. 6D and 6H).

From the results, it could be seen that the PHD1 and 2 genes inhibited cambium activity in vascular bundles and suppressed a mechanism of differentiation from the phloem.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

INDUSTRIAL APPLICABILITY

According to the exemplary embodiments of the present invention, since the development of phloem is remarkably improved when the PHD genes are knocked out or knocked down in a plant, it is expected to improve the functions of the phloem by regulating the expression of the PHD genes using a genetic engineering technique, thereby promoting the development of storage organs in the crops which may be used by human beings.

The invention claimed is:

1. A method of increasing phloem formation in a plant, comprising:

transforming a plant cell with a recombinant VIGS vector comprising a gene encoding a PHD protein to silence a PHD gene, wherein the PHD protein has the amino acid sequence set forth in SEQ ID NO: 2;

generating a transformed plant or plants from the transformed plant cell having increased phloem formation compared to a control plant lacking the vector; and screening the transformed plant or plants comprising the VIGS construct for increased phloem development when compared to a control plant lacking the vector and selecting a plant or plants determined to have increased phloem formation for further treatment or cultivation.

2. The method of claim 1, wherein the transforming step comprises:

inserting a gene encoding a PHD protein into a VIGS vector, wherein the PHD protein has the amino acid sequence set forth in SEQ ID NO: 2;

transforming *Agrobacterium* sp. with the constructed vector; and infiltrating a plant with the transformed *Agrobacterium* sp.

3. The method of claim 2, wherein the plant is selected from the group consisting of rice, wheat, barley, corn, bean, potato, Indian bean, oats, Indian millet, *Arabidopsis thaliana*, Chinese cabbage, radish, red pepper, strawberry, tomato, watermelon, cucumber, cabbage, oriental melon, pumpkin, Welsh onion, onion, carrot, ginseng, a tobacco plant, a cotton plant, sesame, sugar cane, sugar beet, *Perilla* sp., peanut, grape, an apple tree, a pear tree, a jujube tree, a peach tree, a kiwi fruit tree, a grape tree, a citrus fruit tree, a persimmon tree, a plum tree, an apricot tree, a banana tree, rose, gladiolus, gerbera, carnation, chrysanthemum, lily, tulip, ryegrass, red clover, orchard-grass, alfalfa, tall-fescue, and perennial ryegrass.

\* \* \* \* \*

SEQUENCE LISTING

```
<160> NUMBER OF SEQ ID NOS: 8

<210> SEQ ID NO 1
<211> LENGTH: 164
<212> TYPE: PRT
<213> ORGANISM: Arabidopsis thaliana
<220> FEATURE:
<223> OTHER INFORMATION: At3G15680-PHD1 Protein
```

<400> SEQUENCE: 1

```
Met Ser Arg Pro Gly Asp Trp Asn Cys Arg Ser Cys Ser His Leu Asn
1               5                   10                  15

Phe Gln Arg Arg Asp Ser Cys Gln Arg Cys Gly Asp Ser Arg Ser Gly
            20                  25                  30

Pro Gly Gly Val Gly Gly Leu Asp Phe Gly Asn Phe Gly Gly Arg Ala
        35                  40                  45

Met Ser Ala Phe Gly Phe Thr Thr Gly Ser Asp Val Arg Pro Gly Asp
    50                  55                  60

Trp Tyr Cys Thr Val Gly Asn Cys Gly Thr His Asn Phe Ala Ser Arg
65              70                  75                  80

Ser Thr Cys Phe Lys Cys Gly Thr Phe Lys Asp Glu Thr Gly Ala Gly
                85                  90                  95

Gly Gly Gly Gly Gly Ile Gly Gly Pro Ala Met Phe Asp Ala Asp Ile
            100                 105                 110

Met Arg Ser Arg Val Pro Gly Asn Gly Arg Ser Ser Trp Lys Ser
            115                 120                 125

Gly Asp Trp Ile Cys Thr Arg Ile Gly Cys Asn Glu His Asn Phe Ala
        130                 135                 140

Ser Arg Met Glu Cys Phe Arg Cys Asn Ala Pro Arg Asp Phe Ser Asn
145                 150                 155                 160

Arg Thr Ser Phe
```

<210> SEQ ID NO 2
<211> LENGTH: 170
<212> TYPE: PRT
<213> ORGANISM: Arabidopsis thaliana
<220> FEATURE:
<223> OTHER INFORMATION: At5G25490-PHD2 Protein

<400> SEQUENCE: 2

```
Met Asn Arg Pro Gly Asp Trp Asn Cys Arg Leu Cys Ser His Leu Asn
1               5                   10                  15

Phe Gln Arg Arg Asp Ser Cys Gln Arg Cys Arg Glu Pro Arg Pro Gly
            20                  25                  30

Gly Ile Ser Thr Asp Leu Leu Ser Gly Phe Gly Gly Arg Pro Val Ser
        35                  40                  45

Ser Ser Phe Gly Phe Asn Thr Gly Pro Asp Val Arg Pro Gly Asp Trp
    50                  55                  60

Tyr Cys Asn Leu Gly Asp Cys Gly Thr His Asn Phe Ala Asn Arg Ser
65              70                  75                  80

Ser Cys Phe Lys Cys Gly Ala Ala Lys Asp Glu Phe Ser Cys Ser Ser
                85                  90                  95

Ala Ala Ala Thr Thr Gly Phe Met Asp Met Asn Val Gly Pro Arg Arg
            100                 105                 110

Gly Leu Phe Gly Phe Gly Gly Ser Ser Gly Gly Gly Gly Thr Gly
            115                 120                 125

Arg Ser Pro Trp Lys Ser Gly Asp Trp Ile Cys Pro Arg Ser Gly Cys
130                 135                 140

Asn Glu His Asn Phe Ala Ser Arg Ser Glu Cys Phe Arg Cys Asn Ala
145                 150                 155                 160

Pro Lys Glu Leu Ala Thr Glu Pro Pro Tyr
            165                 170
```

<210> SEQ ID NO 3
<211> LENGTH: 495
<212> TYPE: DNA
<213> ORGANISM: Arabidopsis thaliana
<220> FEATURE:
<223> OTHER INFORMATION: At3G15680-PHD1 cDNA

<400> SEQUENCE: 3

```
atgagcagac ccggagattg gaactgcagg tcatgcagcc atctcaactt ccagcgccgt        60
gactcttgcc agcgatgcgg tgactctcgt tccggccccg gtggagttgg tggcttagac       120
tttggtaatt tcggtggcag agccatgtct gctttcggat tcaccaccgg ctccgacgtt       180
cgtcccggtg attggtactg caccgtggga aactgcggga cacacaactt cgccagtcgc       240
tccacctgct tcaaatgcgg cactttcaag gacgagaccg cgctggagg cggaggtggt        300 ggcatcggcg tccggccat gtttgacgcc gacattatgc ggtctagagt ccccggtaac        360
ggtggtcgct ctagctggaa atccggcgac tggatttgca ctaggattgg ttgcaatgag       420
cataactttg caagcagaat ggaatgcttc aggtgcaatg caccaaggga cttcagcaac       480
agaacctctt tctaa                                                         495
```

<210> SEQ ID NO 4
<211> LENGTH: 513
<212> TYPE: DNA
<213> ORGANISM: Arabidopsis thaliana
<220> FEATURE:
<223> OTHER INFORMATION: At5G25490-PHD2 cDNA

<400> SEQUENCE: 4

```
atgaataggc cgggagattg gaactgcaga ttgtgtagcc acctcaactt ccagaggagg        60
gattcatgcc aacgttgtag agagcctaga ccgggcggga tcagtaccga tttactcagc       120
ggttttggtg gccgtccggt tagtagctcc ttcggtttca acaccgggcc cgatgtgcga       180
cccggggatt ggtattgcaa ccttggggat tgtgggacac ataatttgc caataggtcc        240 agttgtttca agtgtggtgc cgcaaaagat gagttttcat gctcaagtgc tgctgcaaca       300
accgggttta tggacatgaa tgttggtccg agacgtggcc ttttggttt tggcggcagc        360 agtagtggtg gtggtggtac gggccgttct ccttggaaat ctggagattg gatttgccca       420
aggtcaggct gtaacgaaca taacttcgca agcaggtcag agtgtttcag gtgtaacgca       480
ccaaaggaac ttgccaccga accaccctat tag                                     513
```

<210> SEQ ID NO 5
<211> LENGTH: 169
<212> TYPE: PRT
<213> ORGANISM: Nicotiana tabacum
<220> FEATURE:
<223> OTHER INFORMATION: NbPHD-PHD Protein

<400> SEQUENCE: 5

```
Met Ser Arg Pro Gly Asp Trp Asn Cys Arg Ser Cys Gln His Leu Asn
1               5                   10                  15

Phe Gln Arg Arg Asp Ser Cys Gln Arg Cys Gly Glu Pro Arg His Gly
            20                  25                  30

His Asp Phe Gly Ser Cys Phe Gly Gly Arg Gly Gly Gly Ser Ser
        35                  40                  45

Ala Phe Gly Phe Asn Thr Gly Pro Asn Val Arg Pro Gly Asp Trp Tyr
    50                  55                  60

Cys Ala Ile Gly Asn Cys Gly Ala His Asn Phe Ala Ser Arg Ser Ser
65                  70                  75                  80
```

```
Cys Phe Lys Cys Gly Ala Phe Lys Asp Asp Ser Ser Gly Gly Gly
                85                  90                  95

Gly Gly Cys Gly Gly Ser Gly Phe Asp Ala Glu His Met Met Ser Ser
            100                 105                 110

Arg Pro Arg Gly Phe Gly Phe Gly Asn Ala Ser Gly Gly Ser Arg Ser
        115                 120                 125

Gly Trp Lys Ser Gly Asp Trp Ile Cys Thr Arg Leu Gly Cys Asn Glu
    130                 135                 140

His Asn Phe Ala Ser Arg Met Glu Cys Phe Arg Cys Asn Ala Pro Arg
145                 150                 155                 160

Asp Ile Ala Gly Asn Lys Ser Ser Tyr
                165
```

<210> SEQ ID NO 6
<211> LENGTH: 155
<212> TYPE: PRT
<213> ORGANISM: Populus nigra
<220> FEATURE:
<223> OTHER INFORMATION: Poplar-PHD Protein

<400> SEQUENCE: 6

```
Met Ser Arg Pro Gly Asp Trp Asn Cys Arg Ser Cys Gln His Leu Asn
1               5                   10                  15

Phe Gln Arg Arg Asp Ser Cys Gln Arg Cys Gly Asp Pro Arg Pro Gly
            20                  25                  30

Glu Arg Asp His Tyr Gly Ser Phe Gly Gly Arg Ser Gly Gly Ser Phe
        35                  40                  45

Gly Phe Thr Gly Pro Asp Val Arg Pro Gly Asp Trp Tyr Cys Ser Val
    50                  55                  60

Gly Asn Cys Gly Ala His Asn Phe Ala Ser Arg Ser Ser Cys Phe Lys
65                  70                  75                  80

Cys Gly Met Ser Lys Asp Glu Ser Ser Gly Gly Gly Leu Asp Ala Asp
                85                  90                  95

Ile Ser Trp Met Arg Gly Tyr Gly Phe Gly Gly Gly Ser Ala Ser Ser
            100                 105                 110

Arg Ser Asn Trp Lys Ser Gly Asp Trp Ile Cys Thr Arg Ser Gly Cys
        115                 120                 125

Asn Glu His Asn Phe Ala Ser Arg Thr Glu Cys Tyr Arg Cys Asn Ala
    130                 135                 140

Pro Arg Glu Ser Gly Ser Asn Lys Ser Ser Tyr
145                 150                 155
```

<210> SEQ ID NO 7
<211> LENGTH: 166
<212> TYPE: PRT
<213> ORGANISM: Zea mays
<220> FEATURE:
<223> OTHER INFORMATION: Maize-PHD Protein

<400> SEQUENCE: 7

```
Met Asn Arg Lys Pro Gly Asp Trp Asp Cys Arg Ala Cys Gln His Leu
1               5                   10                  15

Asn Phe Ser Arg Arg Asp Ala Cys Gln Arg Cys Ser Glu Pro Arg Gly
            20                  25                  30

Val Gly Asp Arg Ser Gly Gly Gly Asp Leu Gly Gly Arg Gly Gly
        35                  40                  45

Ser Ser Phe Gly Gly Gly Phe Gly Ala Gly Ser Asp Val Arg Pro Gly
```

```
                    50                  55                  60

Asp Trp Tyr Cys Ser Cys Gly Ala His Asn Phe Ala Ser Arg Ser Asn
65                  70                  75                  80

Cys Phe Arg Cys Ser Ala Tyr Lys Glu Glu Ala Ala Gly Ala Phe Asp
                    85                  90                  95

Ser Asp Met Ser Arg Ser Arg Gly Tyr Ala Gly Phe Gly Ser Gly Ala
                100                 105                 110

Ala Ala Arg Thr Asn Arg Pro Gly Trp Lys Ser Gly Asp Trp Ile Cys
                115                 120                 125

Thr Arg Ser Gly Cys Asn Glu His Asn Phe Ala Ser Arg Met Glu Cys
                130                 135                 140

Phe Arg Cys Asn Ala Pro Arg Asp Ser Gly Ser Ala Ala Thr Thr Thr
145                 150                 155                 160

Tyr Glu Asn Tyr Leu His
                165

<210> SEQ ID NO 8
<211> LENGTH: 145
<212> TYPE: PRT
<213> ORGANISM: Oryza sp.
<220> FEATURE:
<223> OTHER INFORMATION: Rice - PHD Protein

<400> SEQUENCE: 8

Met Asn Ile Gln Arg Lys Pro Gly Asp Trp Asn Cys Lys Ser Cys Gln
1               5                   10                  15

His Leu Asn Phe Ser Arg Arg Asp Tyr Cys Gln Arg Cys His Thr Pro
                20                  25                  30

Arg Gln Asp Leu Pro Leu Gly Asp Gly Tyr Val Pro Gly Gly Val Leu
            35                  40                  45

Thr Ser Leu Asp Ile Arg Pro Gly Asp Trp Tyr Cys Asn Cys Gly Tyr
        50                  55                  60

His Asn Phe Ala Ser Arg Ala Ser Cys Phe Lys Cys Gly Ala Ile Val
65                  70                  75                  80

Lys Asp Leu Pro Ala Gly Gln Gly Gly Val Ala Asn Gly Asp Phe
                85                  90                  95

Ala Arg Ala Leu Asp Ser Ser Ala Val Arg Ala Gly Trp Lys Ala Gly
                100                 105                 110

Asp Trp Ile Cys Thr Arg Pro Gly Cys Asn Val His Asn Phe Ala Ser
                115                 120                 125

Arg Ile Glu Cys Tyr Arg Cys Asn Ala Pro Arg Glu Ala Gly Asn Val
                130                 135                 140

Lys
145
```